United States Patent
Luo (10) Patent No.: US 6,882,702 B2
(45) Date of Patent: Apr. 19, 2005

(54) INTENSITY MODULATED RADIOTHERAPY INVERSE PLANNING ALGORITHM

(75) Inventor: Chunsong Luo, Miami, FL (US)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 10/424,798

(22) Filed: Apr. 29, 2003

(65) Prior Publication Data
US 2004/0001569 A1 Jan. 1, 2004

Related U.S. Application Data

(60) Provisional application No. 60/375,828, filed on Apr. 29, 2002.

(51) Int. Cl.$^7$ .............................................. A61N 5/10
(52) U.S. Cl. ....................................................... 378/65
(58) Field of Search ........................................... 378/65

(56) References Cited

U.S. PATENT DOCUMENTS

| | | | | |
|---|---|---|---|---|
| 6,038,283 A | * | 3/2000 | Carol et al. ................... | 378/65 |
| 6,260,005 B1 | * | 7/2001 | Yang et al. .................... | 703/11 |
| 6,411,675 B1 | * | 6/2002 | Llacer .......................... | 378/65 |
| 6,560,311 B1 | * | 5/2003 | Shepard et al. ............... | 378/65 |
| 6,714,620 B1 | | 3/2004 | Caflisch et al. | |

\* cited by examiner

Primary Examiner—David V. Bruce
Assistant Examiner—Thomas R Artman
(74) Attorney, Agent, or Firm—Venable LLP; Ann S. Hobbs (57) ABSTRACT

A method in a computer for optimizing a dosage of intensity modulated radiotherapy (IMRT) comprises the steps of: dividing a three dimensional (3D) volume into a grid of dose voxels, wherein each dose voxel receives a dose of radiation from at least one pencil beam having a pencil beam weight and a gantry angle; selecting a first set of dose voxels from the 3D volume positioned within at least one of a planning target volume (PTV), organs at risk (OAR), and normal tissue in a neighborhood of the PTV; choosing a dose matrix from the first set of dose voxels; constructing a beam weight vector of individual beam weights for each pencil beam at each gantry angle; calculating a transfer matrix representing a dose deposition to the dose voxels from each pencil beam with unit beam weight; inverting the transfer matrix; performing a matrix multiplication of the inverted transfer matrix and the dose matrix and populating the beam weight vector with the results of the matrix multiplication; and iteratively modifying a plurality of doses in the dose matrix within a given range, wherein the range has a specific probability distribution function of acceptable dose values, and repeating the matrix multiplication until the negative weights in the beam weight vector are substantially eliminated, resulting in an optimized set of doses.

43 Claims, 9 Drawing Sheets

INTENSITY MODULATED RADIOTHERAPY INVERSE PLANNING ALGORITHM

CROSS-REFERENCE TO RELATED APPLICATIONS

This application claims the benefit of U.S. Provisional Patent Application No. 60/375,828, Confirmation No. 3165, filed Apr. 29, 2002, of common inventorship and assignee, the contents of which are incorporated by reference in their entirety.

BACKGROUND OF THE INVENTION

1. Field of the Invention

The present invention relates generally to optimizing a dosage of intensity modulated radiotherapy (IMRT), and more particularly to minimizing the negative beam in IMRT.

2. Related Art

Intensity modulated radiotherapy (IMRT) is a method of treating cancer that is particularly useful when the cancer is entangled with critical organs, such as the spinal cord. IMRT allows for a balanced dose to the target, i.e. the cancerous area, while sparing the surrounding critical organs.

One of the challenges of IMRT is delivering an effective dosage of radiation to the targeted tissue without harming surrounding tissue and organs. Traditionally, the planning of the treatment has fallen to the radiation oncologist, physicist and dosimetrist, who base their dosage decisions on their experience with expected and achievable doses in the target and surrounding critical organs for a given beam setup.

Optimization algorithms have been developed to assist in the dosage planning. Many of these algorithms were adapted from image reconstruction algorithms. Examples of optimization algorithms include simulated annealing, filtered backprojection, and various other iterative approaches. These algorithms are all iterative, and share one of two common problems. First, stochastic methods are slow to converge on a global minimum solution, and require a great deal of computing time. Second, deterministic methods are faster, but use fewer constraints and do not always find a global minimum solution.

What is needed then is a method of finding a highly optimized dosage for IMRT that does not require a great deal of computing time.

SUMMARY OF THE INVENTION

In an exemplary embodiment of the present invention an inverse planning algorithm for minimizing the negative beam in intensity modulated radiotherapy (IMRT) is disclosed.

In an exemplary embodiment, the present invention can be a method in a computer for optimizing a dosage of intensity modulated radiotherapy (IMRT) comprises the steps of: dividing a three dimensional (3D) volume into a grid of dose voxels, wherein each dose voxel receives a dose of radiation from at least one pencil beam having a pencil beam weight and a gantry angle; selecting a first set of dose voxels from the 3D volume positioned within at least one of a planning target volume (PTV), organs at risk (OAR), and normal tissue in a neighborhood of the PTV; choosing a dose matrix from the first set of dose voxels; constructing a beam weight vector of individual beam weights for each pencil beam at each gantry angle; calculating a transfer matrix representing a dose deposition to the dose voxels from each pencil beam with unit beam weight; inverting the transfer matrix; performing a matrix multiplication of the inverted transfer matrix and the dose matrix and populating the beam weight vector with the results of the matrix multiplication; and iteratively modifying a plurality of doses in the dose matrix within a given range, wherein the range has a specific probability distribution function of acceptable dose values, and repeating the matrix multiplication until the negative weights in the beam weight vector are substantially eliminated, resulting in an optimized set of doses.

In another exemplary embodiment, the present invention can be a computer system that optimizes a dosage of intensity modulated radiotherapy (IMRT) comprising: means for dividing a three dimensional (3D) volume into a grid of dose voxels, wherein each dose voxel receives a dose of radiation from at least one pencil beam having a pencil beam weight and a gantry angle; means for selecting a first set of dose voxels from the 3D volume positioned within at least one of a planning target volume (PTV), organs at risk (OAR), and normal tissue in a neighborhood of the PTV; means for choosing a dose matrix from the first set of dose voxels; means for constructing a beam weight vector of individual beam weights for each pencil beam at each gantry angle; means for calculating a transfer matrix representing a dose deposition to the dose voxels from each pencil beam with unit beam weight; means for inverting the transfer matrix; means for performing a matrix multiplication of the inverted transfer matrix and the dose matrix and populating the beam weight vector with the results of the matrix multiplication; and means for iteratively modifying a plurality of doses in the dose matrix within a given range, wherein the range has a specific probability distribution function of acceptable dose values, and repeating the matrix multiplication until the negative weights in the beam weight vector are substantially eliminated, resulting in an optimized set of doses.

In another exemplary embodiment, the present invention can be a computer useable information storage medium storing computer readable program code for causing a computer to perform the steps of: dividing a three dimensional (3D) volume into a grid of dose voxels, wherein each dose voxel receives a dose of radiation from at least one pencil beam having a pencil beam weight and a gantry angle; selecting a first set of dose voxels from the 3D volume positioned within at least one of a planning target volume (PTV), organs at risk (OAR), and normal tissue in a neighborhood of the PTV; choosing a dose matrix from the first set of dose voxels; constructing a beam weight vector of individual beam weights for each pencil beam at each gantry angle; calculating a transfer matrix representing a dose deposition to the dose voxels from each pencil beam with unit beam weight; inverting the transfer matrix; performing a matrix multiplication of the inverted transfer matrix and the dose matrix and populating the beam weight vector with the results of the matrix multiplication; and iteratively modifying a plurality of doses in the dose matrix within a given range, wherein the range has a specific probability distribution function of acceptable dose values, and repeating the matrix multiplication until the negative weights in the beam weight vector are substantially eliminated, resulting in an optimized set of doses.

BRIEF DESCRIPTION OF THE DRAWINGS

The foregoing and other features and advantages of the invention will be apparent from the following, more particular description of a preferred embodiment of the invention, as illustrated in the accompanying drawings wherein like reference numbers generally indicate identical.

DETAILED DESCRIPTION

A preferred embodiment of the invention is discussed in detail below. While specific exemplary embodiments are discussed, it should be understood that this is done for illustration purposes only. A person skilled in the relevant art will recognize that other components and configurations can be used without parting from the spirit and scope of the invention.

The IMRT optimization algorithm of the present invention is based on the direct inverse operation of linear algebra. The objective function to be optimized is the quadratic summation of negative beam weights. Instead of iterating over the beam weights, as other optimization algorithms do, the method of the present invention iterates the doses in a dose matrix within a given range. Minimizing the objective function effectively searches for the physically achievable beams.

A three dimensional (3D) volume of the target is divided into a grid of dose voxels, where each dose voxel receives a dose of radiation from one or more pencil beams each having a pencil beam weight and a gantry angle. For example, pencil beams can be formed with 1.0 cm by 1.0 cm, 0.5 cm by 0.5 cm, or other sized and shaped beamlets. The radiation can be, for example, photon radiation or proton radiation (called proton beam intensity modulated radiation therapy or PMRT). In PMRT, the intensity and energy of the beams are modulated. From the grid, a set of dose voxels is selected from the planning target volume (PTV), organs at risk (OAR), and normal tissue in a neighborhood of the PTV. The number of dose voxels in the chosen set equals the total number of pencil beams for the 3D volume. For example, using 1.0 cm by 1.0 cm pencil beams, a 15 cm by 15 cm field in ten gantry angles would result in 2,250 pencil beams and dose voxels.

A dose matrix is then selected from the subset of dose voxels. This dose matrix is composed of the dose voxels from an arbitrary selection of dose points from target volumes, critical organs, or surrounding tissues. The dose in each voxel includes primary and internal scatter radiation from all the pencil beams, unlike some algorithms which only deal with primary radiation and produce quite different IMRT plans from those that account for the scattered radiation. The prescription for each category of dose point could contain the given dose range corresponding to the tolerances, biological indices and/or minimum and maximum dose requirements. Since the method of the present invention is a true inverse process, the mathematical beam profile generated in each calculation can produce the desired dose distributions within the designed dose voxels. But the initial mathematical beam profile of the method of the present invention consists of many physically unrealizable negative beam weights. Simply setting those negative beams to zero would leave substantial compensating positive beams and not yield an acceptable plan. Accordingly, the method of the present invention simultaneously iterates doses in a batch of dose voxels within the given dose windows and searches for a physically realizable solution. From the inversely calculated beam weights, the optimization process would gradually minimize the objective function and eventually converge to or approach the global minimum. When the objective function reaches the vicinity of the global minimum, the negative beam weights in the final beam profile are nearly eliminated. The remaining negative beams contribute a small portion of energy in the total spectrum of the beams. Then, zeroing these negative beam weights would not change the calculated result significantly and produce an acceptable plan.

A beam weight vector of individual beam weights for each pencil beam at each gantry angle is populated with the result of a matrix multiplication of a transfer matrix representing a dose deposition to the dose voxels from each pencil beam with unit beam weight, and the dose matrix. The values of the beam weights will be a combination of positive, zero and negative values. Because beams with negative beam weights do not exist, minimizing the negative beam weights, i.e. bringing the values toward zero, will result in a dose matrix of physically achievable beams. The doses in the dose matrix are either randomly and/or deterministically iteratively modified, within specific ranges having specific probability distribution functions, and the matrix multiplication is redone, in order to minimize the negative beam weight values.

The optimization centers around minimizing the summation over the square of each negative beam weight. Such a summation would be computationally expensive, in terms of time, due to the need to screen each beam weight for a negative value. The present invention instead minimizes the sum, over all the beam weights, of each beam weight, multiplied by the difference of the beam weight and its absolute value. When placed in matrix equivalent form, this computation is quickly performed. The random variations in dose voxels ensure that a global minimum, and not just a local minimum, is found or approached.

Figure 1:
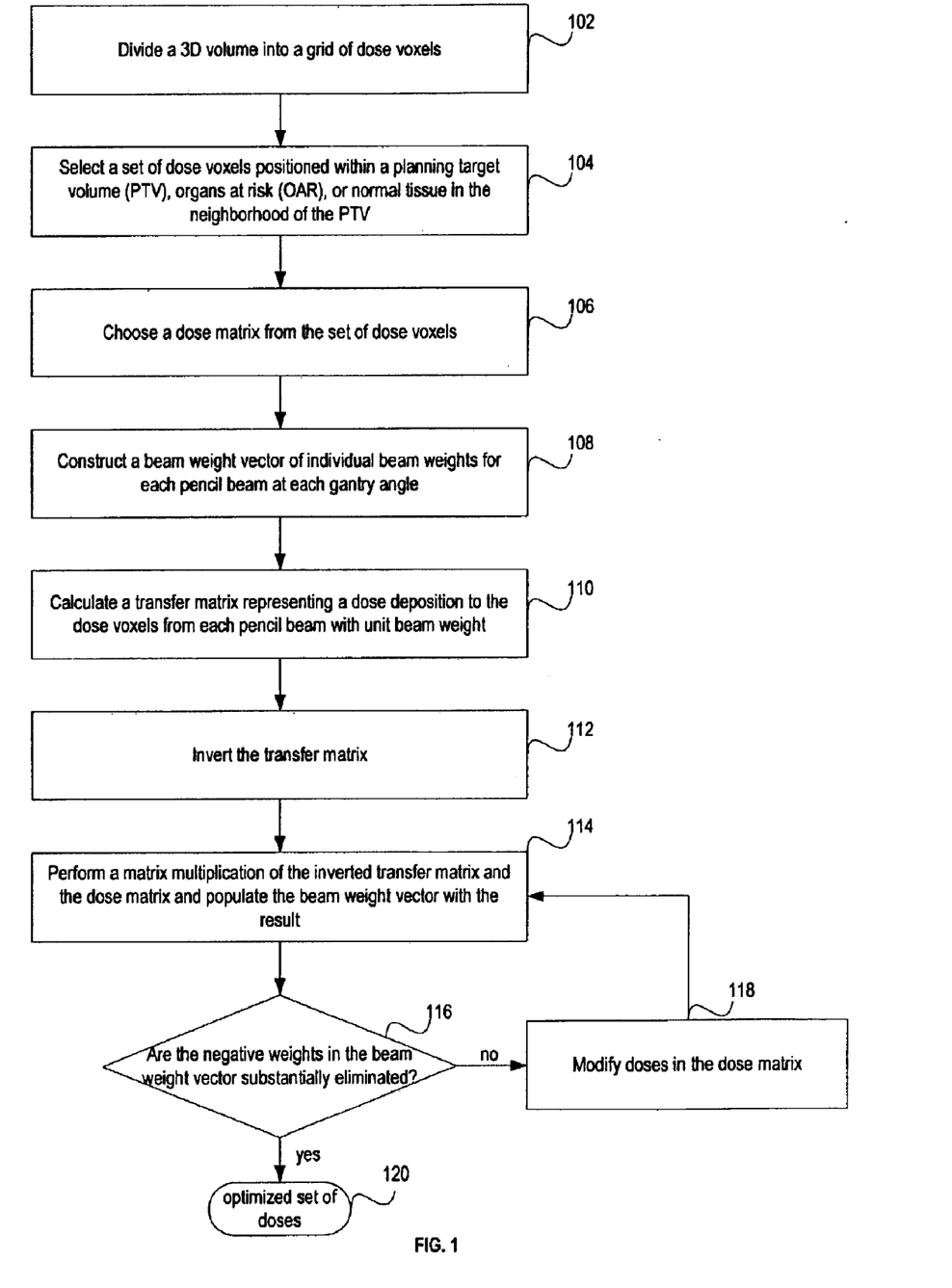
FIG. 1 shows a flowchart of the overall method of the present invention.
Figure 2A:
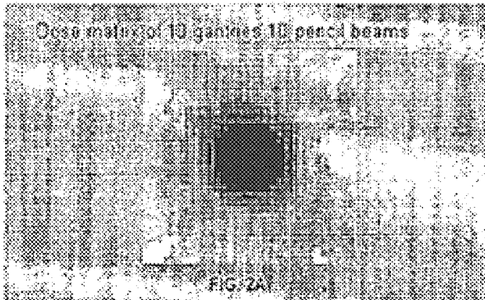
FIG. 2A shows a 1 cm×1 cm grid used in the forward calculation for deriving the transfer matrix for an "R"-shaped target area.
Figure 2B:
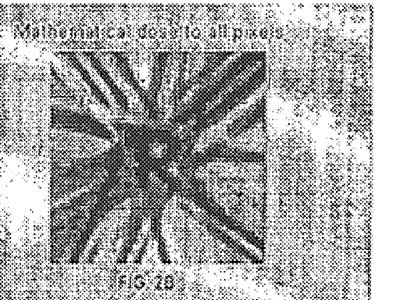
FIG. 2B shows the dose distributions to the all the calculated pixels for the target of a "R"-shaped area in FIG. 2A's setup.
Figure 2C:
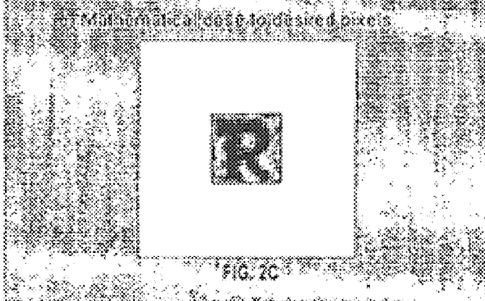
FIG. 2C shows the designated subset of pixels for the target of the "R"-shaped area in FIG. 2A's setup.
Figure 2D:
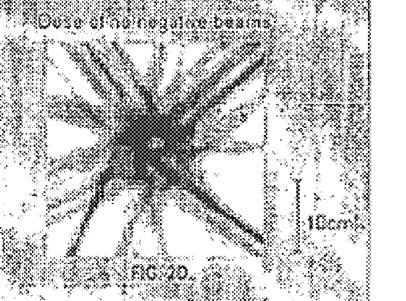
FIG. 2D shows the dose distribution with only physically realizable beams for the target of the "R"-shaped area in FIG. 2A's setup.

FIG. 1 shows a flowchart of the overall method of the present invention. In step 102, a 3D volume is divided into a grid of voxels, for example, with coordinates of (x, y, z). Each voxel receives a total dose of d(x, y, z) from all the pencil beams $w_{nm}$, where $w_{nm}$ corresponds to the pencil beam weight of beamlet m in gantry position n, n=1, ..., N and m=1, ..., M. N is the number of gantry positions and M is the number of pencil beams in each gantry position. Given $t_{nm}(x, y, z)$, representing the dose deposition to voxel (x, y, z) from pencil beam $w_{nm}$ of unit beam weight, then $$d(x, y, z) = \sum_{n=1}^{N} \sum_{m=1}^{M} t_{nm}(x, y, z) w_{nm}. \quad (1)$$

Equation (1) applies to all the voxels within the volume in any grid size. Due to the limited constraints of gantry positions and pencil beams, an inverse solution does not exist that yields $w_{nm}$ from d(x, y, z) for all the voxels. However, as all the beams from the various gantry angles converge onto the target, the tissues far from the target are in low dose regions and automatically protected. If the optimization is only considered in tumor and sensitive tissue regions and leaving normal tissue uncontrolled, it yields better tumor coverage while sparing sensitive organs; the dose to other uncontrolled normal tissues is often still acceptable. Therefore, in step 104, the outermost dose voxels can be left alone and only the set of dose voxels within the target, critical organs and in the immediate neighboring normal tissues are considered. The number of dose voxels is then set to equal the total number of pencil beams. With this subset of dose voxels, a strict mathematical relation is formed from expected doses to beam weights.

In step 106, a dose matrix is selected from the set of dose voxels. Let D be the dose matrix from the subset of dose voxels of arbitrarily selected dose points within the whole dose lattice in the 3D volume. The selected dose points should include points within the planning target volume (PTV), points within the organs at risk (OAR), and points within adjacent normal tissues.

In an exemplary embodiment, the subsets of dose voxels D can be selected as follows: since the 3D volume has been divided into a grid of voxels, let the grid size be 1.0 cm in all directions for a 1.0×1.0 cm² pencil beam setup (set grid size as 0.5 cm if 0.5×0.5 cm² pencil beams are used). The dose at the center of each grid, d(x, y, z) represents the dose point in this voxel. All the voxels enclosed by PTV are counted as dose points for PTV. All the voxels enclosed by OAR are counted as dose points for OAR. The voxels with their centers outside of PTV or OAR, but having contact with PTV or OAR surfaces, are also counted into the corresponding groups, except the voxels within the boundary of PTV with OAR. All the remaining voxels, which are neighbors to the PTV or OAR, and also located within at least one beam path, are counted as dose points for adjacent normal tissues. The simplest method is to use a cubic volume enclosing the PTV and OAR with at least 1.0 cm margin within the borders of this cubic volume. All the voxels within this cube beside voxels for PTV and voxels for OAR are counted as dose points for adjacent normal tissues. Another way to select these dose voxels is to use a conformed shape enclosing the PTV and OAR with enough margin.

The number of selected dose voxel points K is equal to N times M: the number of gantries N multiplied by the number of beamlets in each gantry position. This limits the number of beam weights to the number of dose constraints. The dose point is denoted by k; k=1, ..., K, and K=NM. All these dose points form a column vector:

$$D = (d_1 \; d_2 \ldots d_k \ldots d_K)' \quad (2)$$

where the apostrophe (') indicates matrix transposition.

Once the dose matrix D is selected, a beam weight vector of individual beam weights for each pencil beam at each gantry angle is constructed in step 108. Let W be the vector composed of individual pencil beam weights from each gantry position:

$$W = \begin{bmatrix} \begin{bmatrix} w_{11} \\ \vdots \\ w_{1M} \end{bmatrix} \\ \vdots \\ w_{nm} \\ \vdots \\ \begin{bmatrix} w_{N1} \\ \vdots \\ w_{NM} \end{bmatrix} \end{bmatrix}. \quad (3)$$

In step 110, a transfer matrix is calculated that represents a dose deposition to the dose voxels from each pencil beam with unit beam weight. Let T be the transfer matrix representing the dose deposition per unit beam weight, which is the function of beam quality, geometry, contour, media composition, etc. The transfer matrix can be obtained in Equation (1) with unit beam weights by means of any existing forward dose calculation model. The forward calculation can account for all the beam characteristics, geometry, medium composition and contours. It also considers doses from scattering, leakages, and from inhomogeneities in the medium. For D and W, T would be:

$$T = \begin{bmatrix} t_{1,11} & \cdots & t_{1,1M} & \cdots & t_{1,N1} & \cdots & t_{1,NM} \\ & & & \cdots & & & \\ t_{k,11} & \cdots & t_{k,1M} & \cdots & t_{k,N1} & \cdots & t_{k,NM} \\ & & & \cdots & & & \\ t_{K,11} & \cdots & t_{K,1M} & \cdots & t_{K,N1} & \cdots & t_{K,NM} \end{bmatrix}. \quad (4)$$

With this assumption, the dose calculation for the selected points is represented as $$D = TW. \quad (5)$$

In an exemplary embodiment of the present invention, pairs of gantry angles that are too close to each other (i.e., within one degree) are avoided. Opposing beams having identical medium composition are also avoided, as are dose points far from any beam. Dose points located outside of the patient's body are excluded. These exclusions prevent the transfer matrix from being singular. In practice, there is no need to select gantry angles close each other, and fewer gantry angles are chosen for an IMRT treatment to save planning as well as treatment time. The number of gantry angles has been investigated in the literature and it was shown that adequate dose distributions could be achieved with only a few gantry angles. Most current clinical applications choose an odd number of gantry angles, typically 5 to 9 gantry positions, so that the opposed gantry angles are avoided.

The beam weights are then expressed with the inversion, in step 112, of this non-singular transfer matrix:

$$W = T^{-1} D \qquad (6)$$

T is a square matrix with positive entries. Its inversion can be calculated, for example, using Gauss-Seidel iteration. For a given D, there is a corresponding mathematical solution of W, composed of positive, zero and negative numbers. Simply setting the negative weights to zero in W would not guarantee an acceptable dosage plan. If the absolute values of all the negative weights were much smaller than the positive ones, then zeroing those negative beams would not change the dose distribution dramatically and it would generate an acceptable plan. By iterating the doses in D within the given range, the following objective function can be minimized:

$$SUM_{neg} = \sum_{uv} w_{uv}^2, \text{ here } w_{uv} < 0 \text{ and } u \in [1, \ldots, N], v \in [1, \ldots, M]. \qquad (7)$$

The foundation of this objective function is the quadratic summation of the negative beam weights, compared to the desired negative beam weights, which are zero. Equation (7) has a theoretical global minimum, although whether it approaches zero depends on the specific problem as well as the setup. A practical solution may approach this theoretical global minimum, but not reach it, due to the time limitation for a reasonable number of iterations. Equation (7) deals with the subset of the beam weights and needs screening for the negative beam weights, which calls for more computing time. The matrix multiplication of step 114 is therefore performed instead with the following equivalent matrix form, which dramatically reduces the calculation time:

$$SUM_{neg} = \frac{1}{2} \sum_{\substack{u=1,\ldots,N \\ v=1,\ldots,M}} w_{uv}(w_{uv} - |w_{uv}|) = \frac{1}{2} W'(W - |W|). \qquad (8)$$

The dose prescriptions are designed with dose ranges for the various regions of interests (ROI):

$$d_{TV,min} \leq d(x, y, z) \leq d_{TV,max}, \text{ if } (x, y, z) \text{ is within the target volume (TV);} \qquad (9)$$

$$0 \leq d(x, y, z) \leq d_{OAR,max}, \text{ if } (x, y, z) \text{ is within the OAR volume;} \qquad (10)$$

$$0 \leq d(x, y, z) \leq d_{ADJ,max}, \text{ if } (x, y, z) \text{ is within adjacent normal tissue.} \qquad (11)$$

Forms (9) to (11) are for the typical ROIs. The number of the ROIs is unlimited. The probability distribution functions within these ranges can be defined based either on the desired volume histograms or on biological dose-response information. If the negative weights in the beam weight vector have not been substantially eliminated at step 116, the next step 118 is to iterate the doses to randomly selected points in D for a "gain" or "loss" based on these ranges and probability distribution functions. In an exemplary embodiment, uniform probability distribution functions are used.

The probability distributions within these ranges can be achieved by subdividing these ROIs into a few corresponding subdivisions, each with its dose range required by the dose-volume histograms (DVH) or derived dose constraints from biological dose response indices. The subdivisions can be formed in either geometrically subdivided regions or/and randomly grouped dose voxels. If biological dose response information is utilized, only the geometrical division would be appropriate to assign the dose constraints to the corresponding tissue types. The subdivisions are defined in each trail and not changed during the iterations, as those are a part of the prescriptions. For example, the following are dose constraints for two subdivisions for each category of the ROIs:

$$d_{TV,min} \leq d(x, y, z) \leq d_{TV,mid}, \qquad (12)$$

if (x, y, z) is within the sub-target volume #1, which is composed of α percent of the target;

$$d_{TV,min} \leq d(x, y, z) \leq d_{TV,max}, \qquad (13)$$

if (x, y, z) is within the sub-target volume #2, which is composed of 100-α percent of the target;

$$0 \leq d(x, y, z) \leq d_{OAR,mid}, \qquad (14)$$

if (x, y, z) is within the sub-OAR volume #1, which is composed of β percent of OAR;

$$0 \leq d(x, y, z) \leq d_{OAR,max}, \qquad (15)$$

if (x, y, z) is within the sub-OAR volume #2, which is composed of 100-β percent of OAR;

$$0 \leq d(x, y, z) \leq d_{ADJ,mid}, \qquad (16)$$

if (x, y, z) is within sub-adjacent normal tissue volume #1, which is composed of δ percent of adjacent normal tissue;

$$0 \leq d(x, y, z) \leq d_{ADJ,max}, \qquad (17)$$

if (x, y, z) is within sub-adjacent normal tissue volume #2, which is composed of 100-δ percent of adjacent normal tissue, here α, β, δ∈[1, 100], $d_{TV,min} < d_{TV,mid} < d_{TV,max}$, $0 < d_{OAR,mid} < d_{OAR,max}$ and $0 < d_{ADJ,mid} < d_{ADJ,max}$.

Let $(^l)$ represent the $l^{th}$ iteration, then the $l^{th}$ result is from the last iteration plus the changes:

$$W^{(l)} = T^{-1}(D^{(l-1)} + \Delta D^{(l)}) = W^{(l-1)} + T^{-1} \Delta D^{(l)} \qquad (18)$$

In each cycle of iteration, a randomly selected group of dose points $d_{k(i)}$ is selected, where i∈[f, g] is the group size; f is the minimum number of dose points in the group and g is the maximum number of dose points in the group; and $d_k$ is the corresponding dose point in D. Assuming h points at this time, the column vector has non-zeros only for these h points:

$$\Delta D^{(l)} = \begin{bmatrix} \vdots \\ \Delta d_{u(1)} \\ \vdots \\ \Delta d_{q(i)} \\ \vdots \\ \Delta d_{v(h)} \\ \vdots \end{bmatrix}. \quad (19)$$

Equation (6) only needs to be calculated once; for subsequent iterations, only a small portion of the terms need to be calculated based on Equation (18). Additionally, most of the elements in Vector (19) are zero. Instead of calculating all the terms in $T^{-1}\Delta D^{(l)}$, only the corresponding column vectors with non-zero dose changes in $T^{-1}$ need to be calculated. The corresponding column vectors are $f_u = (f_{1,u} f_{2,u} \ldots f_{K,u})'$, ..., $f_q = (f_{1,q} f_{2,q} \ldots f_{K,q})'$, ..., $f_v = (f_{1,v} f_{2,v} \ldots f_{K,v})'$. Then $$\Delta W^{(l)} = \quad (20)$$

$$T^{-1}\Delta D^{(l)} = \begin{bmatrix} \sum (f_{1,u}\Delta d_{u(1)} + \ldots + f_{1,q}\Delta d_{q(i)} + \ldots + f_{1,v}\Delta d_{v(h)}) \\ \vdots \\ \sum (f_{K,u}\Delta d_{u(1)} + \ldots + f_{K,q}\Delta d_{q(i)} + \ldots + f_{K,v}\Delta d_{v(h)}) \end{bmatrix}.$$

Since negative weights may change within the beamlets from one iteration to another, it is not possible to screen out negative beamlets. Equation (18) needs to be calculated each time with the result of the last iteration and calculated result of Equation (20).

The initializations start with setting all the target voxels to the prescribed dose; the rest of the voxels are set to zero dose. However, the initial doses can take any set of values from the corresponding dose ranges bounded by Forms (9)–(11) or (12)–(17). In each iteration, the doses in the randomly selected group of dose voxels in D are changed by a pre-selected small "gain." This "gain" carries a randomly selected sign that changes from voxel to voxel within the group that determines the "gain" to be added to or subtracted from the existing dose. The resulting dose has to meet the dose constraints of Forms (9)–(11) or (12)–(17), otherwise the "gain" will not be applied to this dose point. The negative beam components are evaluated with objective function (8). If this iteration causes the objective function to decrease after a repetition of step 114, then this group of doses is accepted. If the iteration causes the objective function to increase, the iterated doses will be kept or discarded, depending on the following probability assessment. The probability is $p = \exp(-\Delta SUM^2/\underline{KT})$ where $\underline{K}$ is the Boltzmann constant and $\underline{T}$ is the temperature, analogous with simulated annealing in thermodynamics; $\Delta SUM$ is the difference between the current $SUM_{neg}$ and the best $SUM_{neg}$ achieved so far. This iteration result is kept to prevent the iteration from being trapped in a local minimum potential, and to give an escaping momentum to jump out from the local minimum and converge to the global minimum.

The speed and the state of convergence have a lot to do with the iteration scheme. Iterating a randomly selected group of dose points in each cycle is the preferred scheme in the exemplary embodiment. Iterating a randomly selected group of dose points in D would tend to make the objective function converge to the global minimum even without applying the escaping momentum (no probability assessment; discard the result which causes the objective function to increase). In contrast, iterating only a single, randomly selected dose point at each cycle would sometimes cause the system to converge to a local minimum, without the application of the escaping momentum. Additionally, iterating a group of dose points in each iteration cycle also decreases the iteration time. For example, the iteration time for a given value of objective function drops to one third when iterating a group of about 10 to 30 randomly selected dose points in each cycle of iteration compared to the time needed for iterating a single randomly selected dose point in each cycle of iteration.

Among the stochastic annealing processes, the following techniques can improve performance. Manipulation of $\underline{KT}$ will change the simulated annealing cooling schemes as well as the speed, and ensure that the iteration converges to the global minimum. Also, selection of a gradually decreasing "gain" will change the convergence speed.

The minima of the objective function are problem and setup specific, as are their convergence properties. The global minimal value of the objective function depends on the prescriptions and beam setup. For a given treatment beam setup, the more physically unachievable the prescriptions are, the higher the value of the global minimum at which the objective function will rest, and the more the final plan will deviate from the prescriptions. The global minimum could be a large value for a certain setup, and even it is reached, the result may not be acceptable. Alternatively, the global minimum may be close to zero, however, it could take a long time to reach. In an exemplary embodiment, the iteration can stop either after a predetermined number of iteration cycles or at a predetermined value difference of the objective function when further iteration would not significantly reduce the value of the objective function. In these curtailed iterations, the iteration may stop at a region near the global or even at a local minimum, and the result generated would be sub-optimal.

The minimum value of the quadratic summation of negative beam weights depends on many factors similar to that of the dose based objective functions. These factors are the total number of beamlets in the setup, the given dose constraints in the prescription Forms (9) to (11) or Forms (12)–(17), as well as the target and OAR shapes, beam energies and geometries. For example, with 9 or 10 gantry positions, and with average target doses normalized to 100 percent, and OAR and adjacent normal tissue maximum doses less than 100 percent, the minimum values of the summation of quadratic negative beam weights can go as low as the range of ten. With these minimum values of the objective functions, the results with the negative beams set to zero would generally yield a reasonable plan. Whether the final plan is acceptable is subject to the clinician's evaluation. Early termination of the iterations may be needed for those cases where the objective function stays high and unchanged. This might indicate that modification to gantry orientations or dose prescriptions may be needed. The final dose distribution could be calculated with Equation (1) for the resulting beam weights with as high resolution as needed.

FIGS. 2–8 illustrate various applications of the method of the present invention using a 2-dimensional inverse problem as a test model. The optimization algorithm presented was tested in many cases with hypothetical targets in a cylindrical phantom. In the test setup, ten beams each with 10 beamlets (10×1 array) in different gantry angles were used. The elementary 1×1 cm$^2$ photon beam is used as a pencil beam; each pencil beam was modeled with an exponential energy deposition kernel and with exponential percent depth dose function for 6MV photons. The pencil beam model is invariant and rotationally symmetric along its axis. The isocenter of the beams is set at the center of a cylindrical phantom. All the pencil beams are assumed to be parallel to the gantry central axis.

Although 2-D inverse planning is presented, the method is in a general form and is true for 3-D. In 2-D, the dose distribution is in a single tomographic plane and the sources of the pencil beams at each gantry angle form a 1-D strip oriented orthogonally to the gantry axis. The algorithm also assumes that the treatment volume has enough axial thickness and uniformity for lateral buildup. These assumptions simplify and ease the derivation of the working module of the algorithm.

FIG. 2 shows a hypothetical "R" shaped target within the cylindrical phantom. Three critical structures were within the "belly" and between the "legs," and out to the middle right "leg" of the "R." The rest of the areas were set as neighboring structures. The gantry angles were integer multiples of 39°, 39*n°, where n=0, 1, 2 . . . 10 and 0° is at the top. In particular, FIG. 2A shows a 1 cm×1 cm grid used in the forward calculation for deriving the transfer matrix. FIG. 2B shows the mathematical dose distributions to the all the calculated pixels. FIG. 2C shows the mathematical dose distribution to the designated subset of pixels. FIG. 2D shows the dose distribution with only physically realizable beams. FIGS. 2B–2D were calculated with smaller grids.

Figure 3A:
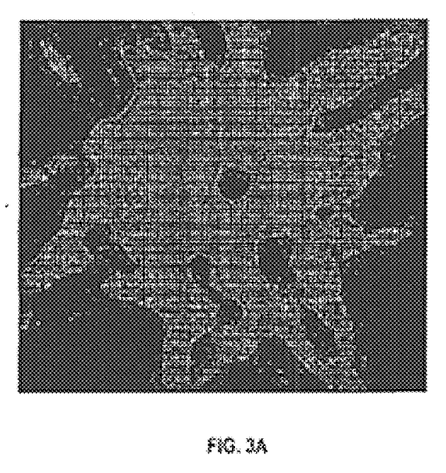
FIG. 3A shows a normalized dose distribution verification for an "R"-shaped target with Kodak verification film.
Figure 3B:
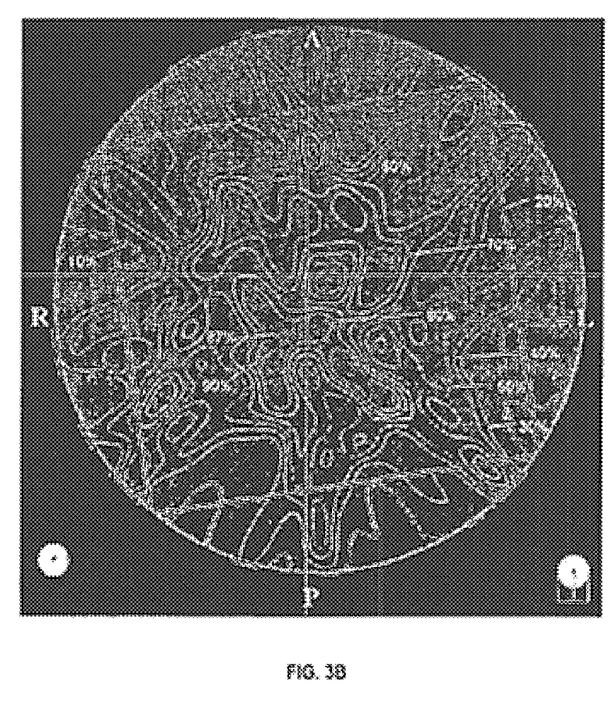
FIG. 3B shows the corresponding dose pattern generated with the calculated beam weight results in the CORVUS planning system's verification module using the intensity map calculated in FIG. 2D.

The verification was performed in a Varian 2100CD accelerator and with a 6MV photon beam. The simulated beam weight results were translated into the leaf-sequencing files by CORVUS software (NOMOS Corporation, Sewickley, Pa.) for step-and-shoot IMRT. A cylindrical phantom was used in the setup, with the Kodak therapy verification film sandwiched in. The result is shown in FIG. 3A, which shows a normalized dose distribution verification for an "R"-shaped target with Kodak verification film. The square area corresponds to the regions in the film measurement. For comparison, FIG. 3B shows the corresponding dose pattern generated with the calculated beam weight results in the CORVUS planning system's verification module (CORVUS verification plan) using the intensity map calculated in FIG. 2D.

FIG. 4 shows calculated results for a prostate-shaped target with 9 gantry orientations of 40°, 80°, 120°, 160°, 200°, 240°, 280°, 320° and 360°. It is a "prostate-shaped" target with the rectum as the critical organ. FIG. 4A shows the dose pattern of unit beam weight of all the pencil beams used in the forward calculation for deriving the transfer matrix, calculated with 1 cm×1 cm grid. FIG. 4B shows the mathematical dose distribution to all the calculated pixels. FIG. 4C shows the mathematical dose distribution to the designated subset of pixels. FIG. 4D shows the dose distribution with only physically realizable beams. FIGS. 4B and 4D were calculated with smaller grids.

Figure 4A:
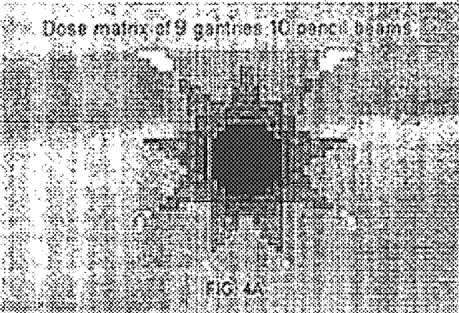
FIG. 4A shows the dose pattern of unit beam weight of all the pencil beams used in the forward calculation for deriving the transfer matrix for the gantry and beam setup.
Figure 4B:
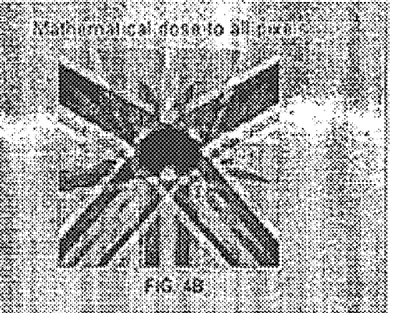
FIG. 4B shows the dose distribution to all the calculated pixels for the target of a prostate-shaped area in FIG. 4A's setup.
Figure 4C:
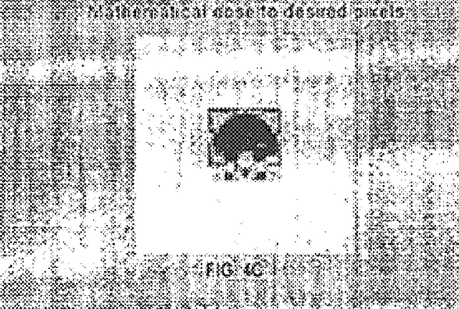
FIG. 4C shows the dose distribution to the designated subset of pixels for the target of the prostate-shaped area in FIG. 4A's setup.
Figure 4D:
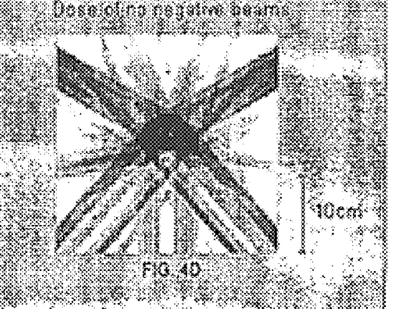
FIG. 4D shows the dose distribution with only physically realizable beams for the target of the prostate-shaped area in FIG. 4A's setup.
Figure 5A:
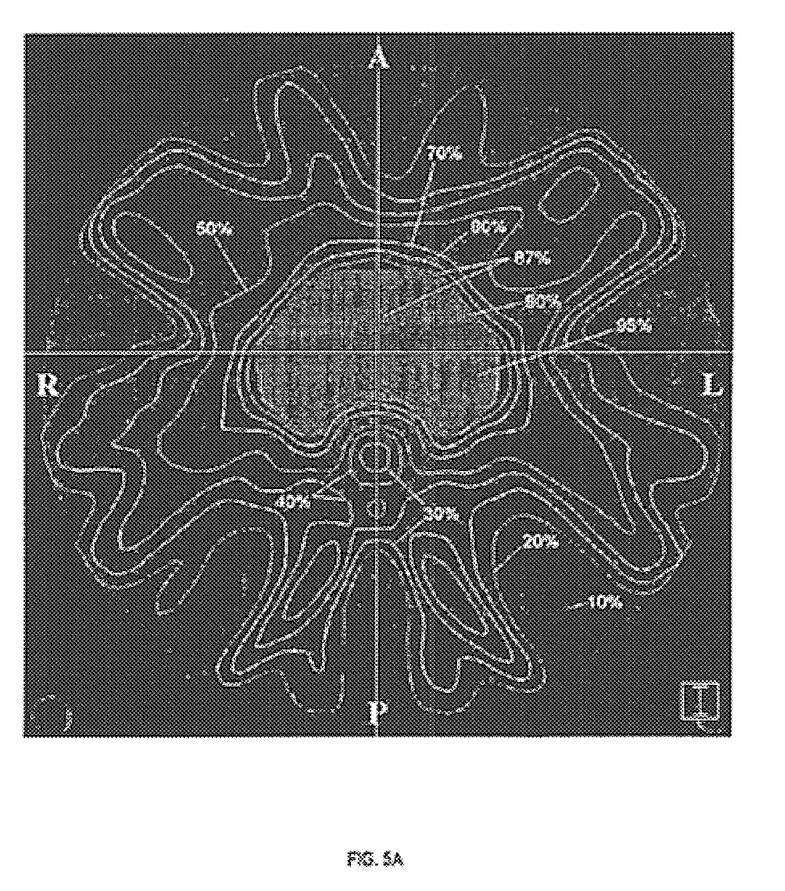
FIG. 5A shows the dose pattern generated in the CORVUS verification module with the presenting algorithm calculated beam weight results in FIG. 4D.
Figure 5B:
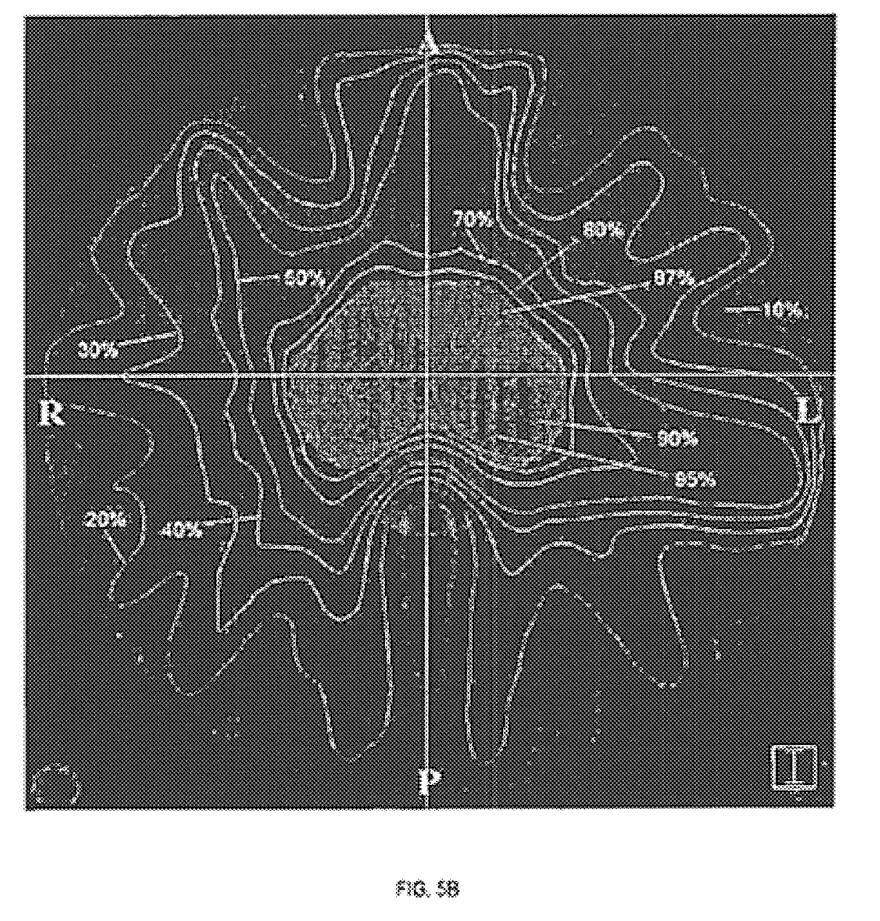
FIG. 5B shows the best result generated in the CORVUS planning system (its optimization algorithm: simulated annealing) chosen from different trails with the same 2 cm superior to inferior target lengths as in FIG. 5A.

FIG. 5A shows the dose pattern generated in the CORVUS verification module with the presenting algorithm calculated beam weight results in FIG. 4D. For comparison, FIG. 4B shows the dose patterns generated with the CORVUS planning system itself (pure simulated annealing algorithm) for the same prostate target and rectum in the same energy and geometry setup, as well as similar dose constraints of targeting PTV dose 180 cGy as those used in FIG. 5A. FIG. 5B shows the best result chosen from different trails with the same 2 cm superior to inferior target lengths as in FIG. 5A.

Figure 6:
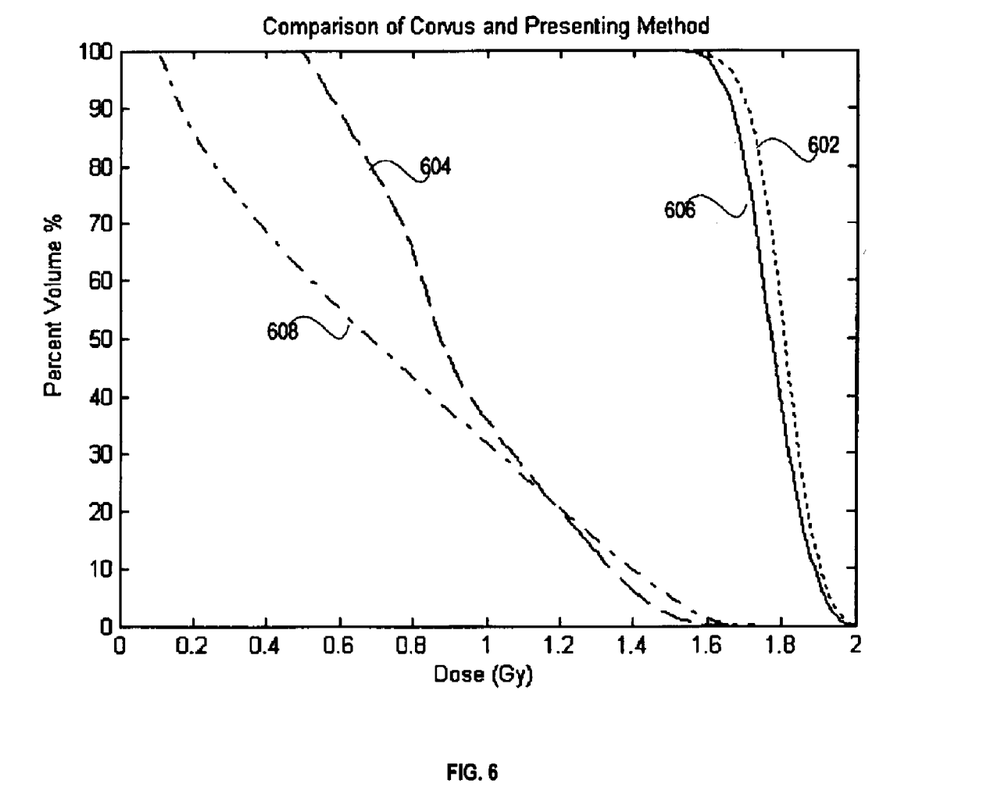
FIG. 6 shows the dose-volume histograms corresponding to FIGS. 5A and 5B.

FIG. 6 shows the corresponding dose-volume histograms. In comparison, the plan achieved from the method of the present invention presents a more conformed, and uniform target dose coverage above the minimum, as well as gives lower maximum dose to the rectum. The dot (602) and the dash (604) lines are the DVHs of the method of the present invention plan; the solid (606) and the dash-dot (608) lines are the DVHs of the CORVUS plan. The comparison of the verification results from either film measurements or from the CORVUS verification plans shows excellent agreement with the overall patterns of the computer-simulated results. Nevertheless, distinct differences may be pointed out even without comparing the isodose lines. These differences are mainly due to using parallel pencil beams to approximate the fan beams and using simple mathematical functions to approximate the real physical beam profiles. However, the focus of the present work is on demonstrating the feasibility and working principles of the optimization algorithm, rather than on a precise match of the beam profile with the analytical functions.

The algorithms with dose based objective functions yield a single set of objective doses to the target, to OARs or the neighboring tissues, and calculate the differences with respect to the delivered doses. Sometimes multiplying factors are used to modify their own importance within the objective function.

Their dose range or percent differences are related to those single objective doses and used to constrain the outcome of the iteration. The method of the present invention prescribes the range of objective doses to the corresponding targets, OARs and neighboring tissues. The relative importance of the specific dose for a ROI is through direct modification of those dose ranges or to the dose distribution within the ranges. This method pays attention to the cooperative effect of the dose voxels on the beamlets, allowing the dose to deviate from the prescription by a given range, and searching for the optimal combined realizable beam profiles.

The calculation of the transfer matrix is more favorable for heterogeneous conditions—this is an intrinsic advantage. Therefore, the method works even better under true beam conditions from its primary ray trace to its full lateral transport as well as leakage and scatter radiation.

The method of the present invention is not limited to isocentric setups; it could be applied in general to non-isocentric and non-coplanar setups. Also, the gantry could be oriented in any direction as long as opposing gantry orientations are avoided for which the ray traces are symmetrical with respect to the isocenter, and by avoiding gantry angles less than one degree apart. Considering the pencil beam's crossing profiles and its superposition properties, the grid size of the selected dose voxel is normally chosen to be the same as the size of the pencil beam. However, the size of the selected dose voxels could also be smaller than the size of the pencil beams if the number of the dose voxels is sufficient to cover the target and OAR for a given number of gantry orientations. The dose uniformity and border conformity in the corresponding ROI are better when the size of the dose voxels in the ROI are smaller than the size of the pencil beams.

Figure 7A:
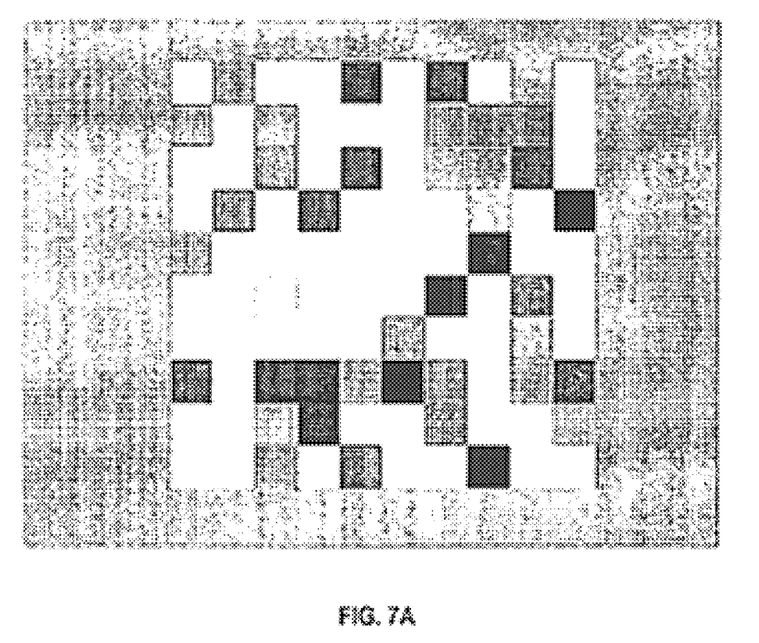
FIG. 7A shows the intensity map of an "R"-shaped target.
Figure 7B:
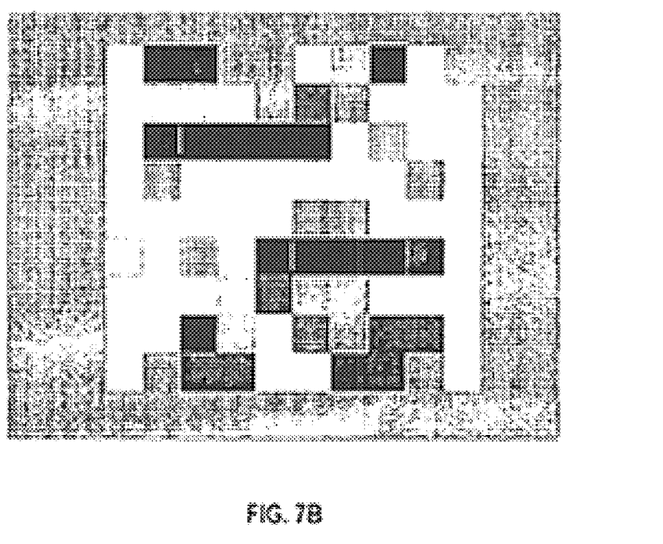
FIG. 7B shows the intensity map of a prostate-shaped target.

The test results show that the beam profiles of each gantry position greatly depend on the nature of the target. FIG. 7A shows the intensity map of an "R"-shaped target; the corresponding gantry angles from top row down are 39°, 78°, 117°, 156°, 195°, 234°, 273°, 312°, 351° and 30° respectively. FIG. 7B shows the intensity map of a prostate-shaped target, corresponding gantry angles from top row down are 40°, 80°, 120°, 160°, 200°, 240°, 280°, 320° and 360° respectively. It is more continuous from one beamlet to the adjacent beamlet for a target having a rather solid shape in the center (FIG. 7B); it is shown to be less continuous for a target with narrow width and hollow interior, as shown in FIG. 7A.

Figure 8A:
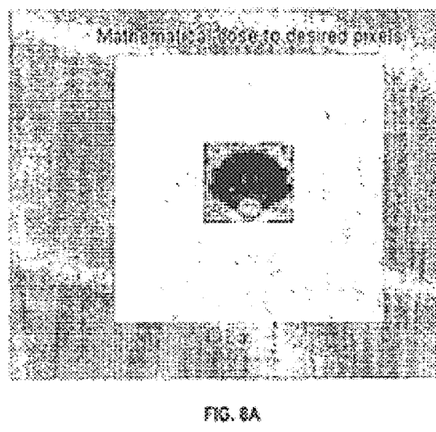
FIGS. 8A–8D show the calculated dose patterns of the prostate shaped target and rectum organ at risk with the dose constraints in different gantry orientations.
Figure 8B:
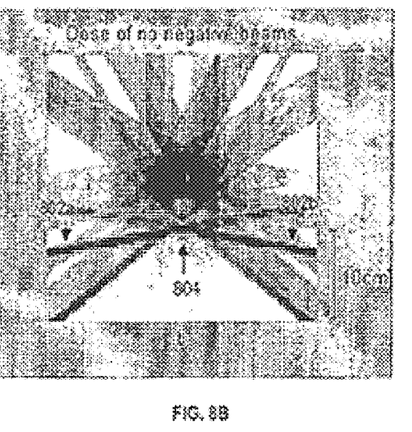
Figure 8C:
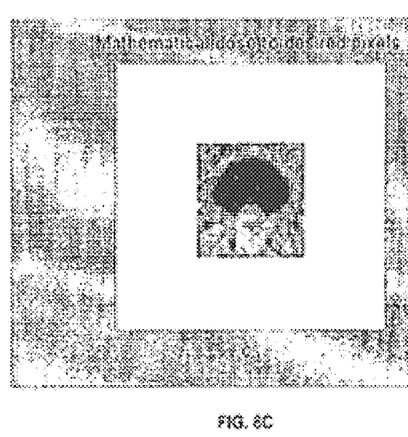
Figure 8D:
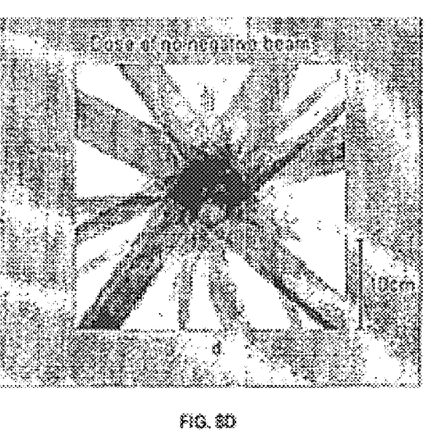

The selection of a subset of dose voxels greatly affects the outcome of the resulting plans. The method would generate a tightly conforming plan to a complex target and OAR structure, but sometimes it does produce sparking hot spots in areas outside the designated subset of the voxels, which are not accounted for during the optimization process. FIGS. 8A–8D show the calculated dose patterns of the same prostate shaped target and rectum OAR of FIGS. 4, 5 and 7B with the same dose constraints in different gantry orientations. In FIGS. 8A and 8B, with 9 gantry orientations each with 10 pencil beams, the arrows indicate the "sparking" hot spots. FIGS. 8C and 8D have 13 gantry orientations each with 12 pencil beams. The hot spots are produced by beam crossings in those regions, indicated by arrows 802a and 802b in FIG. 8B, or by beams used to neutralize the negative doses outside the target, indicated by arrow 804 in FIG. 8B. The hot spots generated by neutralizing beams outside the target can be easily eliminated by canceling all the beams whose ray tracks are located outside the target. It is a concern if those hot spots were generated by beams whose ray tracks pass through the target and contribute dose to the target. This might be unacceptable for certain cases. Such problems might be overcome by relocating some of the designated voxels to those regions, by changing the gantry orientations or even by increasing the size of the subset, as seen in FIGS. 8C and 8D. The total number of the practically resolvable dose voxels remains approximately the same for a given case, but the total number of determining variables, the number of pencil beams, can be increased as more gantry positions are added. Subsequently, the total number of the subset of designated dose voxels increases accordingly. With this increased subset of dose voxels, more area will be covered and the covered area will be extended far beyond the high dose gradient region. In those cases, better dose uniformity with less sparking hot spots should be seen in regions beyond the targets.

When the quadratic summation of negative beam weights falls to the range of ten or even closer to zero, the value of this objective function changes much more slowly since the objective value reaches the region of a flat bottom. Further increase in the iteration cycles does not significantly improve the value of the objective function. Termination of the iteration is more reasonable in those stages. However, the features of the final dose plan are related to the composition of those negative beams. Since removing the negative beams will expose the overdoses in some voxels, the overdose patterns directly reflect the amounts and the locations of the negative beams. If the value of this objective function were mainly contributed by either one, or a few beamlets, then the dose plan would have only one or a few compensating spikes. In other words, trade-off from early termination of the iterations may produce higher deviations in the negative beam distribution. Sometimes, it is case and setup specific.

Since the doses in the dose matrix D in each iteration are bounded by constrained doses of Forms (9)–(11) or (12)–(17), the negative beams in solution from Equation (6) bring down the doses in some overdosed voxels, as long as D is resting at a physically unachievable combination. Realistically, almost all the dose constraints given for IMRT are more or less physically unachievable. However, the clinician would accept the IMRT plan that does not deviate much from what was asked for. The method of the present invention looks for the exact physically achievable plan that deviates minimally from the given dose constraints. The final plan would have its minimum, or a value close to the minimum, of the quadratic summation of negative beam weights. The physically achievable plan sets to zero those negative beams from the final plan. Unlike other algorithms, which zero the negative beams during the iteration process, zeroing the negative beams is the final step of this method. When the iteration process approaches the vicinity of the global minimum, the absolute values of the negative weights are much smaller than the positive ones and these negative beams mainly located in the OAR and normal tissue regions especially located in their boundaries to the target. Zeroing these small negative beams will remove the negative dose components in the dose voxels and cause doses to increase by a small amount corresponding to the weights of those negative beams mainly in regions of the OAR or normal tissues. This dose increment may cause some voxels having doses above the corresponding upper constraints, the overdoses; in most cases this is acceptable since the maximum dose limits for OAR or normal tissues were set lower to begin with. This dose increase in the target is not a concern since it is mainly from the scatter dose components of those removed negative beams.

Finally, all the points have doses equal or above the corresponding minima bounded by Equations (9)–(11) or (12)–(17) since the doses lower than the corresponding minimum constraints are never accepted during the iterations. Since the minimum target dose is decisive for eradication of a tumor, the guaranteed lower target dose limit is a very important feature of this method compared to other algorithms. The amount of overdose in a voxel suppressed by the negative dose components is proportional to the negative beam weights. The smaller the absolute value of negative beam weights, the smaller are the overdoses. Therefore, these overdoses in D overall are the least, since the total value of the quadratic negative beam weights is the least. This situation is not worse than the situation in any other IMRT algorithm, in which the final plan must accept some doses beyond the prescriptions.

The speed of stochastic iteration is a naturally slow process. The major advantage of stochastic iteration is that it converges to the global minimum. With an 850 MHz laptop personal computer, the current test setups with 9 or 10 gantry angles, each with 10×1 beamlets take about 30 minutes to converge. This is acceptable for a stochastic iteration approach. One of the following factors or their combinations could solve the 3D problem with the stochastic approach within a reasonable time: (1) the forward portion using existing fast calculation engines; (2) hardware with higher speed and parallel processors; (3) software using robust coding; or (4) using network computing. Further improvement in speed will depend on the introduction of new iteration schemes, such as the deterministic approach for the algorithm.

While various embodiments of the present invention have been described above, it should be understood that they have been presented by way of example only, and not limitation. Thus, the breadth and scope of the present invention should not be limited by any of the above-described exemplary embodiments, but should instead be defined only in accordance with the following claims and their equivalents.

What is claimed is:

1. A method in a computer for optimizing a dosage of intensity modulated radiotherapy (IMRT) comprising:

dividing a three dimensional (3D) volume into a grid of dose voxels, wherein each dose voxel receives a dose of radiation from at least one pencil beam having a pencil beam weight and a gantry angle;

selecting a first set of dose voxels from said 3D volume positioned within at least one of a planning target volume (PTV), organs at risk (OAR), and normal tissue in a neighborhood of said PTV;

choosing a dose matrix from said first set of dose voxels;

constructing a beam weight vector of individual beam weights for each pencil beam at each gantry angle;

calculating a transfer matrix representing a dose deposition to the dose voxels from each pencil beam with unit beam weight;

inverting said transfer matrix;

performing a matrix multiplication of said inverted transfer matrix and said dose matrix and populating said beam weight vector with the results of said matrix multiplication; and iteratively modifying a plurality of doses in said dose matrix within a given range, wherein said range has a specific probability distribution function of acceptable dose values, and repeating said matrix multiplication until the negative weights in said beam weight vector are substantially eliminated, resulting in an optimized set of doses.

2. The method of claim 1, wherein said iterative modification is performed in at least one of a random and a deterministic manner.

3. The method of claim 2, wherein, when a random modification is used, a gain having a randomly selected sign is applied to a dose to modify said dose, and when said modified dose is not within said given range, said dose is not modified by said gain.

4. The method of claim 2, wherein said step of iteratively modifying a plurality of doses in at least one of a random and a deterministic manner is repeated for a pre-determined number of iterations.

5. The method of claim 2, wherein said step of iteratively modifying a plurality of doses in at least one of a random and a deterministic manner is repeated until the values of said summation of negative beam weights has reached a pre-determined value.

6. The method of claim 1, wherein said given range of acceptable dose values is selected from a range of doses for said PTV, a range of doses for OAR and a range of doses for normal tissue in a neighborhood of said PTV, and wherein said probability distribution functions within the said ranges are determined from the requirements of at least one of dose volume histograms and biological dose-response indices.

7. The method of claim 1, wherein the method is used in at least one of an isocentric setup, a non-isocentric setup, and a non-coplanar setup.

8. The method of claim 1, wherein the method is used in at least one of a homogeneous medium and a heterogeneous medium.

9. The method of claim 1, wherein said dose of radiation received by each dose voxel includes primary and internal scatter radiation from all of said pencil beams.

10. The method of claim 1, wherein the number of dose voxels in said first set equals the total number of pencil beams for said 3D volume.

11. The method of claim 1, wherein the dose deposition to the dose voxels from each pencil beam with unit beam weight is a function of at least one of a beam quality, geometry, contour, and media composition.

12. The method of claim 1, wherein said transfer matrix is not singular.

13. The method of claim 1, wherein a pair of gantry angles that are within one degree of each other are not used.

14. The method of claim 1, wherein the size of said selected dose voxels is smaller than the size of said pencil beams if the number of dose voxels is sufficient to cover both said PTV and OAR.

15. The method of claim 1, wherein all doses are equal to or greater than a corresponding minimum in said given range.

16. A computer system that optimizes a dosage of intensity modulated radiotherapy (IMRT) comprising:

means for dividing a three dimensional (3D) volume into a grid of dose voxels, wherein each dose voxel receives a dose of radiation from at least one pencil beam having a pencil beam weight and a gantry angle;

means for selecting a first set of dose voxels from said 3D volume positioned within at least one of a planning target volume (PTV), organs at risk (OAR), and normal tissue in a neighborhood of said PTV;

means for choosing a dose matrix from said first set of dose voxels;

means for constructing a beam weight vector of individual beam weights for each pencil beam at each gantry angle;

means for calculating a transfer matrix representing a dose deposition to the dose voxels from each pencil beam with unit beam weight;

means for inverting said transfer matrix;

means for performing a matrix multiplication of said inverted transfer matrix and said dose matrix and populating said beam weight vector with the results of said matrix multiplication; and means for iteratively modifying a plurality of doses in said dose matrix within a given range, wherein said range has a specific probability distribution function of acceptable dose values, and repeating said matrix multiplication until the negative weights in said beam weight vector are substantially eliminated, resulting in an optimized set of doses.

17. The system of claim 16, wherein said iterative modification is performed in at least one of a random and a deterministic manner.

18. The system of claim 17, wherein, when a random modification is used, said means for iteratively modifying further comprises means for applying a gain having a randomly selected sign to a dose to modify said dose, and when said modified dose is not within said given range, said dose is not modified by said gain.

19. The system of claim 16, wherein said given range of acceptable dose values is selected from a range of doses for said PTV, a range of doses for OAR and a range of doses for normal tissue in a neighborhood of said PTV, and wherein said probability distribution functions within the said ranges are determined from the requirements of at least one of dose volume histograms and biological dose-response indices.

20. The system of claim 16, wherein the system is used in at least one of an isocentric setup, a non-isocentric setup, and a non-coplanar setup.

21. The system of claim 16, wherein the system is used in at least one of a homogeneous medium and a heterogeneous medium.

22. The system of claim 16, wherein said dose of radiation received by each dose voxel includes primary and internal scatter radiation from all of said pencil beams.

23. The system of claim 16, wherein the number of dose voxels in said first set equals the total number of pencil beams for said 3D volume.

24. The system of claim 16, wherein the dose deposition to the dose voxels from each pencil beam with unit beam weight is a function of at least one of a beam quality, geometry, contour, and media composition.

25. The system of claim 16, wherein said transfer matrix is not singular.

26. The system of claim 16, wherein a pair of gantry angles that are within one degree of each other are not used.

27. The system of claim 16, wherein the size of said selected dose voxels is smaller than the size of said pencil beams if the number of dose voxels is sufficient to cover both said PTV and OAR.

28. The system of claim 16, wherein all doses are equal to or greater than a corresponding minimum in said given range.

29. A computer useable information storage medium storing computer readable program code for causing a computer to perform the steps of:

dividing a three dimensional (3D) volume into a grid of dose voxels, wherein each dose voxel receives a dose of radiation from at least one pencil beam having a pencil beam weight and a gantry angle;

selecting a first set of dose voxels from said 3D volume positioned within at least one of a planning target volume (PTV), organs at risk (OAR), and normal tissue in a neighborhood of said PTV;

choosing a dose matrix from said first set of dose voxels;

constructing a beam weight vector of individual beam weights for each pencil beam at each gantry angle;

calculating a transfer matrix representing a dose deposition to the dose voxels from each pencil beam with unit beam weight;

inverting said transfer matrix;

performing a matrix multiplication of said inverted transfer matrix and said dose matrix and populating said beam weight vector with the results of said matrix multiplication; and iteratively modifying a plurality of doses in said dose matrix within a given range, wherein said range has a specific probability distribution function of acceptable dose values, and repeating said matrix multiplication until the negative weights in said beam weight vector are substantially eliminated, resulting in an optimized set of doses.

30. The computer useable information storage medium of claim 29, wherein said iterative modification is performed in at least one of a random and a deterministic manner.

31. The computer useable information storage medium of claim 30, wherein, when a random modification is used, a gain having a randomly selected sign is applied to a dose to modify said dose, and when said modified dose is not within said given range, said dose is not modified by said gain.

32. The computer useable information storage medium of claim 30, wherein said step of iteratively modifying a plurality of doses in at least one of a random and a deterministic manner is repeated for a pre-determined number of iterations.

33. The computer useable information storage medium of claim 30, wherein said step of iteratively modifying a plurality of doses in at least one of a random and a deterministic manner is repeated until the values of said summation of negative beam weights has reached a pre-determined value.

34. The computer useable information storage medium of claim 29, wherein said given range of acceptable dose values is selected from a range of doses for said PTV, a range of doses for OAR and a range of doses for normal tissue in a neighborhood of said PTV, and wherein said probability distribution functions within the said ranges are determined from the requirements of at least one of dose volume histograms and biological dose-response indices.

35. The computer useable information storage medium of claim 29, wherein the method is used in at least one of an isocentric setup, a non-isocentric setup, and a non-coplanar setup.

36. The computer useable information storage medium of claim 29, wherein the method is used in at least one of a homogeneous medium and a heterogeneous medium.

37. The computer useable information storage medium of claim 29, wherein said dose of radiation received by each dose voxel includes primary and internal scatter radiation from all of said pencil beams.

38. The computer useable information storage medium of claim 29, wherein the number of dose voxels in said first set equals the total number of pencil beams for said 3D volume.

39. The computer useable information storage medium of claim 29, wherein the dose deposition to the dose voxels from each pencil beam with unit beam weight is a function of at least one of a beam quality, geometry, contour, and media composition.

40. The computer useable information storage medium of claim 29, wherein said transfer matrix is not singular.

41. The computer useable information storage medium of claim 29, wherein a pair of gantry angles that are within one degree of each other are not used.

42. The computer useable information storage medium of claim 29, wherein the size of said selected dose voxels is smaller than the size of said pencil beams if the number of dose voxels is sufficient to cover both said PTV and OAR.

43. The computer useable information storage medium of claim 29, wherein all doses are equal to or greater than a corresponding minimum in said given range.

* * * * *